United States Patent
Henley (10) Patent No.: US 10,676,466 B2
(45) Date of Patent: Jun. 9, 2020

(54) CRYSTALLINE HYDRATE OF THE COMPOUND (2S,3R)-ISOPROPYL 2-(((2-(1,5-DIMETHYL-6-OXO-1,6-DIHYDROPYRIDIN-3-YL)-1-((TETRAHYDRO-2H-PYRAN-4-YL) METHYL)-1H-BENZO[D]IMIDAZOL-5-YL)METHYL)AMINO)-3-HYDROXY-BUTANOATE EDISYLATE

(71) Applicant: GLAXOSMITHKLINE INTELLECTUAL PROPERTY DEVELOPMENT LIMITED, Brentford, Middlesex (GB)

(72) Inventor: Nicholas Paul Henley, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 16/326,970

(22) PCT Filed: Aug. 31, 2017

(86) PCT No.: PCT/EP2017/071867
§ 371 (c)(1),
(2) Date: Feb. 21, 2019

(87) PCT Pub. No.: WO2018/041946
PCT Pub. Date: Mar. 8, 2018

(65) Prior Publication Data
US 2019/0177307 A1   Jun. 13, 2019

(30) Foreign Application Priority Data
Sep. 2, 2016 (GB) .................... 1614939.5

(51) Int. Cl.
*C07D 405/14* (2006.01)
*A61P 19/02* (2006.01)

(52) U.S. Cl.
CPC ............ *C07D 405/14* (2013.01); *A61P 19/02* (2018.01); *C07B 2200/13* (2013.01)

(58) Field of Classification Search
None
See application file for complete search history.

(56) References Cited

U.S. PATENT DOCUMENTS

2015/0051208 A1   2/2015 Engelhardt et al.

FOREIGN PATENT DOCUMENTS

WO    WO 2016/146738 A1    9/2016

OTHER PUBLICATIONS

Garnier et al. "BET bromodomain inhibitors: a patent review," Expert Opinion on Therapeutic Patents 2013. (Year: 2013).*
Wadhwa et al. "Bromodomain Inhibitor Review: Bromodomain and Extra-terminal Family Protein Inhibitors as a Potential New Therapy in Central Nervous System Tumors," Cureus 8(5) 1-8. (Year: 2014).*

* cited by examiner

Primary Examiner — Jeffrey S Lundgren
Assistant Examiner — Michael J Schmitt
(74) Attorney, Agent, or Firm — Robert J. Smith (57) ABSTRACT

The present invention relates to a crystalline hydrate of the compound (2S,3R)-isopropyl 2-(((2-(1,5-dimethyl-6-oxo-1,6-dihydropyridin-3-yl)-1-((tetrahydro-2H-pyran-4-yl) methyl)-1H-benzo[d]imidazol-5-yl)methyl)amino)-3-hydroxybutanoate edisylate and to its use in the treatment of various disorders for which a BET inhibitor is indicated, in particular inflammatory and autoimmune diseases, and cancers. Processes for the manufacture of this crystalline form and pharmaceutical compositions comprising the crystalline form are also disclosed and form part of the present invention.

9 Claims, 4 Drawing Sheets

CRYSTALLINE HYDRATE OF THE COMPOUND (2S,3R)-ISOPROPYL 2-(((2-(1,5-DIMETHYL-6-OXO-1,6-DIHYDROPYRIDIN-3-YL)-1-((TETRAHYDRO-2H-PYRAN-4-YL)METHYL)-1H-BENZO[D]IMIDAZOL-5-YL)METHYL)AMINO)-3-HYDROXY-BUTANOATE EDISYLATE

This application is a § 371 of International Application No. PCT/EP2017/071867, filed 31 Aug. 2017, which claims the priority of GB Application No. GB 1614939.5, filed 2 Sep. 2016.

FIELD OF THE INVENTION

The present invention relates to a crystalline hydrate of the compound (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate and to its use in the treatment of various disorders for which a BET inhibitor is indicated, in particular inflammatory and autoimmune diseases, and cancers. Processes for the manufacture of this crystalline hydrate form and pharmaceutical compositions comprising the crystalline hydrate form are also disclosed and form part of the present invention.

BACKGROUND TO THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, and SUMOylation. These epigenetic marks are written and erased by specific enzymes, which place tags on specific residues within the histone tail, thereby forming an epigenetic code, which is then interpreted by the cell to allow regulation of gene expression.

Histone acetylation is most usually associated with the activation of gene transcription, as the modification relaxes the interaction of the DNA and the histone octomer by changing the electrostatics. In addition to this physical change, specific proteins recognise and bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et al, *J Med. Chem.* 2011, 54, 3827-3838).

Inhibiting the binding of a BET protein to acetylated lysine residues has the potential to ameliorate progression of several diseases, including but not limited to, cancer (Dawson M. A. et al, *Nature,* 2011: 478(7370):529-33; Wyce, A. et al, *Oncotarget.* 2013: 4(12):2419-29), sepsis (Nicodeme E. et al, *Nature,* 2010: 468(7327):1119-23), autoimmune and inflammatory diseases such as rheumatoid arthritis and multiple sclerosis (Mele D. A. et al, *Journal of Experimental Medicine,* 2013: 210(11):2181-90), heart failure (Anand P. et al, *Cell,* 2013: 154(3):569-82), and lung fibrosis (Tang X. et al, *Molecular Pharmacology,* 2013: 83(1): 283-293).

There exists a need in the art for further chemical compounds which inhibit the activity of bromodomains, in particular compounds that inhibit the binding of BET family bromodomain containing proteins to acetylated lysine residues. In particular, there is a need for compounds that possess an improved profile over known BET inhibitors.

International Patent Application No. PCT/EP2016/055792 discloses a crystalline form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate.

SUMMARY OF THE INVENTION

The present invention in a first aspect provides a crystalline hydrate of the compound (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, which is a BET inhibitor and may thus be useful for the treatment of various disorders for which a BET inhibitor is indicated, in particular inflammatory and autoimmune diseases, and cancers.

In a further aspect, the present invention provides a pharmaceutical composition comprising said crystalline hydrate of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, together with one or more pharmaceutically acceptable excipients.

In a further aspect, the present invention provides a crystalline hydrate of the compound (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, for example a monohydrate, for use in therapy, and in particular for use in the treatment of a disease or condition for which a BET inhibitor in indicated, such as autoimmune and/or inflammatory disease (e.g. rheumatoid arthritis or osteoarthritis) and cancers.

In yet a further aspect, the present invention provides a method of treatment of a disease or condition for which a BET inhibitor is indicated, such as autoimmune and/or inflammatory disease (e.g. rheumatoid arthritis or osteoarthritis) and cancers, which method comprises administering to a subject in need thereof a therapeutically effective amount of a crystalline hydrate of the compound (2S,3R)-isopropyl 2-(((2-(1,5-dimethyl-6-oxo-1,6-dihydropyridin-3- yl)-1-((tetrahydro-2H-pyran-4-yl)methyl)-1H-benzo[d]imidazol-5-yl)methyl)amino)-3-hydroxybutanoate edisylate.

DETAILED DESCRIPTION OF THE INVENTION

Definitions

As used herein, the term "bromodomain" refers to evolutionary and structurally conserved modules (approximately 110 amino acids in length) that bind acetylated lysine residues, such as those on the N-terminal tails of histones. They are protein domains that are found as part of much larger bromodomain containing proteins (BCPs), many of which have roles in regulating gene transcription and/or chromatin remodelling. The human genome encodes for at least 57 bromodomains.

As used herein, the term "BET" refers to the bromodomain and extraterminal domain family of bromodomain containing proteins which include BRD2, BRD3, BRD4 and BRDt.

As used herein, the term "BET inhibitor" refers to a compound that is capable of inhibiting the binding of one or more BET family bromodomain containing proteins (e.g. BRD2, BRD3, BRD4 or BRDT) to, for example, acetylated lysine residues.

As used herein, the term "edisylate" refers to the United States Adopted Name (USAN) approved contraction for 1,2-ethandisulfonate.

It will be appreciated that many organic compounds can form complexes with solvents in which they are reacted or from which they are precipitated or crystallised. These complexes are known as "solvates". When the compound forms a complex with water, this is referred to as a "hydrate". References herein to "hydrate" include, for example, hemi-hydrate, monohydrate, sesquihydrate, dihydrate and trihydrate. In one embodiment, the crystalline hydrate is a monohydrate.

As used herein, the term "treatment" refers to prophylaxis of the condition, ameliorating or stabilising the specified condition, reducing or eliminating the symptoms of the condition, slowing or eliminating the progression of the condition, and preventing or delaying reoccurrence of the condition in a previously afflicted patient or subject.

As used herein, the term "therapeutically effective amount" refers to the quantity of a compound of formula (I), or a pharmaceutically acceptable salt thereof, which will elicit the desired biological response in an animal or human body.

As used herein, the term "subject" refers to an animal or human body.

It is to be understood that references herein to "compound(s) of the invention" mean a crystalline hydrate of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate.

STATEMENT OF THE INVENTION

In a first aspect, the present invention provides a crystalline hydrate of the compound (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, which is a BET inhibitor and may thus be useful for the treatment of various disorders for which a BET inhibitor is indicated, in particular inflammatory and autoimmune diseases, and cancers.

International Patent Application No. PCT/EP2016/055792 describes two preparations of the compound (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate, of formula (I) (Example 303)

(I)

PCT/EP2016/055792 further describes the preparation and characterisation of a crystalline form of the 1,2-ethanedisulfonic acid salt of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate, of formula (II):

(II)

A new crystalline hydrate of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate has now been found.

The crystalline hydrate described herein has been characterised by X-ray powder diffraction (XRPD), differential scanning calorimetry (DSC), Raman spectroscopy and thermogravimetric analysis (TGA).

Instrument Details

X-Ray Powder Diffraction (XRPD)

The data were acquired on a PANalytical X'Pert Pro powder diffractometer, model PW3040/60 using an X'Celerator detector. The acquisition conditions were: radiation: Cu $K_\alpha$, generator tension: 40 kV, generator current: 45 mA, start angle: 2.0° 2θ, end angle: 40.0° 2θ, step size: 0.01670 2θ, time per step: 31.75 seconds. The sample was prepared by mounting a few milligrams of sample on a silicon wafer (zero background plate), resulting in a thin layer of powder.

FT-Raman Spectroscopy

Raman spectrum was collected with a Nicolet NXR 9650 spectrometer (Thermo Scientific) equipped with 1064 nm Nd:YVO$_4$ excitation laser, liquid nitrogen cooled Ge detector and a microstage. Spectrum was acquired at 4 cm$^{-1}$ resolution, 128 scans, using Happ-Genzel apodization function and 2-level zero-filling. Band positions were determined using Omnic software and the margin of error in each band position is approximately ±1 cm$^{-1}$.

Differential Scanning Calorimetry (DSC)

DSC thermogram was obtained with a TA Instruments Q200 differential scanning calorimeter equipped with an autosampller and a refrigerated cooling system under 50 ml/min N$_2$ purge. DSC thermogram was obtained in a crimped aluminium pans at 10.00° C./min.

Thermogravimetric Analysis (TGA)

TGA thermogram was obtained with a TA Instruments Q5000 thermogravimetric analyser under 50 mL/min N$_2$ purge at 10° C./min.

Figure 1:
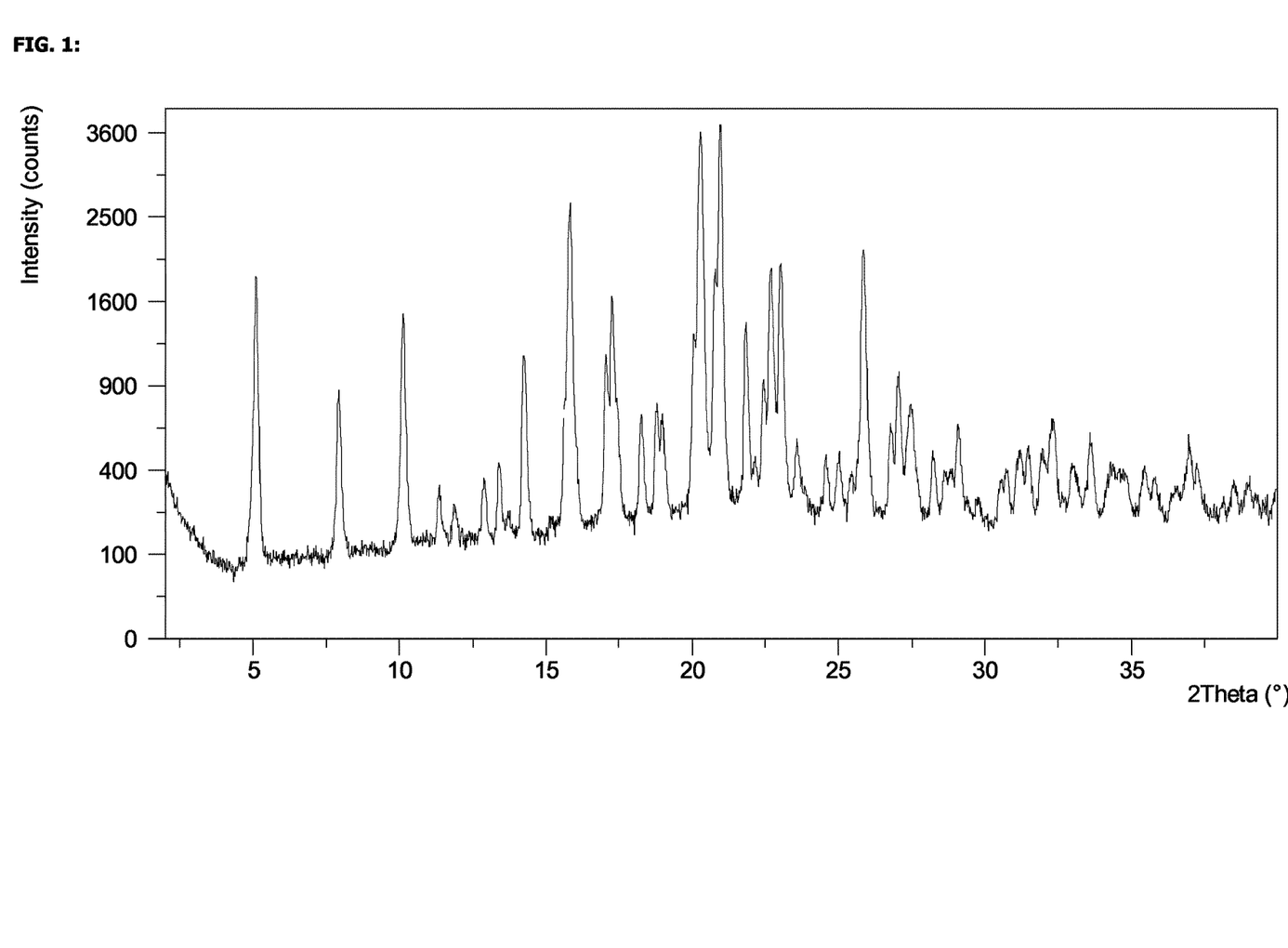
FIG. 1 shows an X-ray powder diffraction pattern of the compound of the invention.

In one embodiment, there is provided a crystalline form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate monohydrate, which has an X-ray powder diffraction pattern substantially as shown in FIG. 1.

Characteristic XRPD angles and d-spacings for Example 4 are recorded in Table 1. The margin of error is approximately ±0.1° 2θ for each of the peak assignments. Peak intensities may vary from sample to sample due to preferred orientation. Peak positions were measured using PANalytical Highscore Plus software.

TABLE 1

X-ray Powder Diffraction (XRPD) Specific
Peaks for the hydrate of Example 4
Example 4

| 2θ/° | d-spacings/Å |
|---|---|
| 5.1 | 17.3 |
| 7.9 | 11.2 |
| 10.1 | 8.7 |
| 11.3 | 7.8 |
| 11.9 | 7.5 |
| 12.9 | 6.9 |
| 13.4 | 6.6 |
| 14.2 | 6.2 |
| 18.3 | 4.9 |
| 20.3 | 4.4 |
| 21.0 | 4.2 |
| 21.8 | 4.1 |

In a further embodiment, there is provided a crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, which has an X-ray powder diffraction pattern with specific peaks at 2θ values, ±0.1° 2θ experimental error, of 5.1, 7.9, 10.1, 11.3, 11.9, 12.9, 13.4, 14.2, 18.3, 20.3, 21.0, and 21.8 degrees, as shown in Table 1.

In another further embodiment, there is provided a crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, which has an X-ray powder diffraction pattern with at least nine specific peaks at 2θ values, ±0.1° 2θ experimental error, selected from a group consisting of 5.1, 7.9, 10.1, 11.3, 11.9, 12.9, 13.4, 14.2, 18.3, 20.3, 21.0, and 21.8 degrees.

In another further embodiment, there is provided a crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, which has an X-ray powder diffraction pattern with at least eight or at least seven or at least six or at least five or at least four specific peaks at 2θ values, ±0.1° 2θ experimental error, selected from a group consisting of 5.1, 7.9, 10.1, 11.3, 11.9, 12.9, 13.4, 14.2, 18.3, 20.3, 21.0, and 21.8 degrees.

In another further embodiment, there is provided a crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, which has an X-ray powder diffraction pattern with at least three specific peaks at 2θ values, ±0.1° 2θ experimental error, selected from a group consisting of 5.1, 7.9, 10.1, 11.3, 11.9, 12.9, 13.4, 14.2, 18.3, 20.3, 21.0, and 21.8 degrees.

Figure 2:
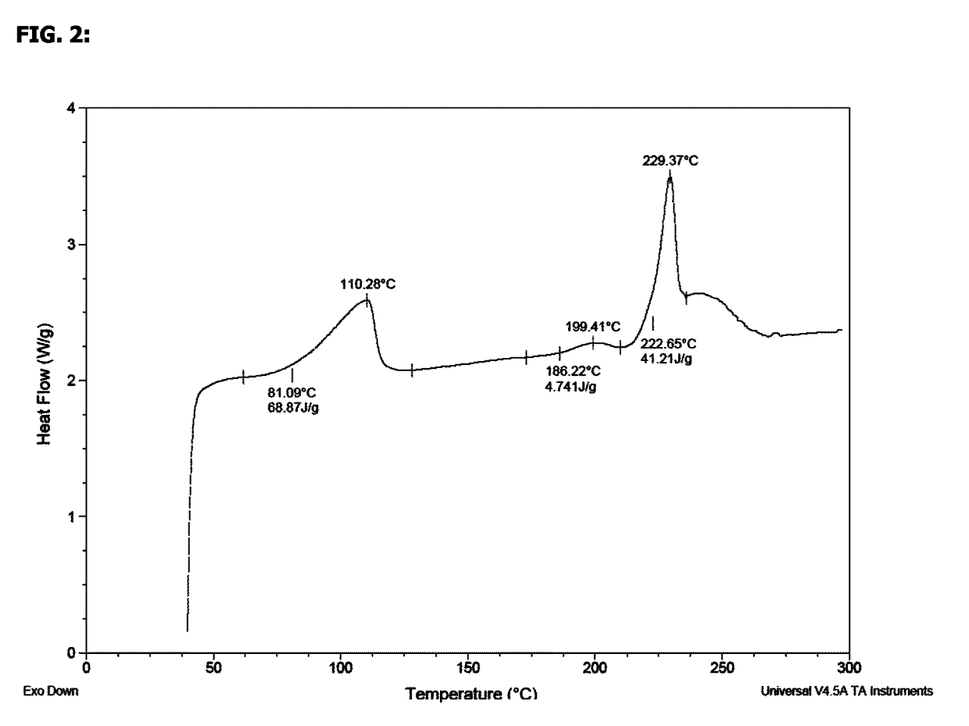
FIG. 2 shows a differential scanning calorimetry thermogram of the compound of the invention.

In a further embodiment, there is provided a crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, which has a DSC thermogram substantially as shown in FIG. 2.

In a further embodiment, there is provided a crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, which has an onset of melting at about 223° C. as determined by DSC.

Figure 3:
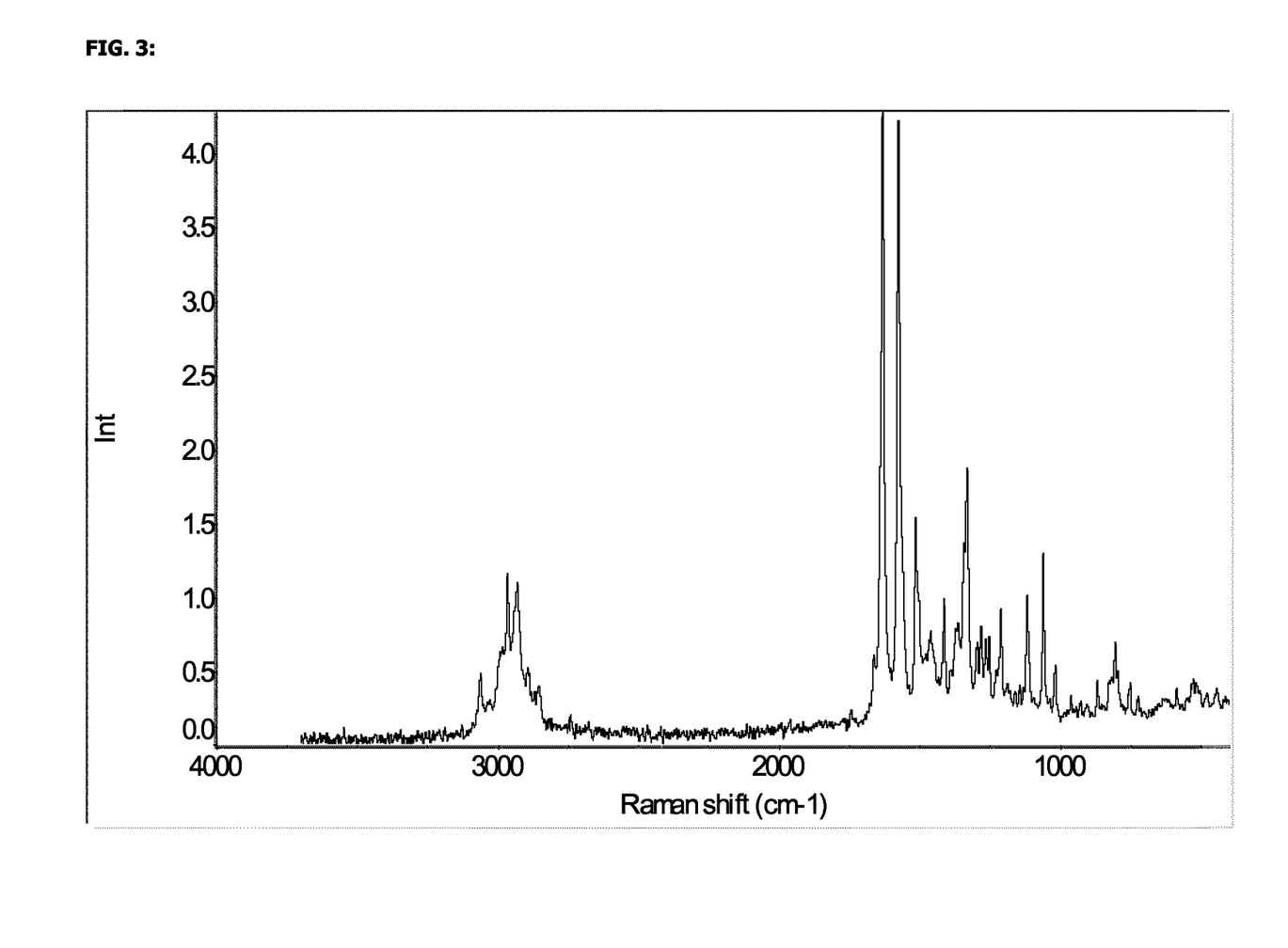
FIG. 3 shows a Raman spectrum of the compound of the invention.
Figure 4:
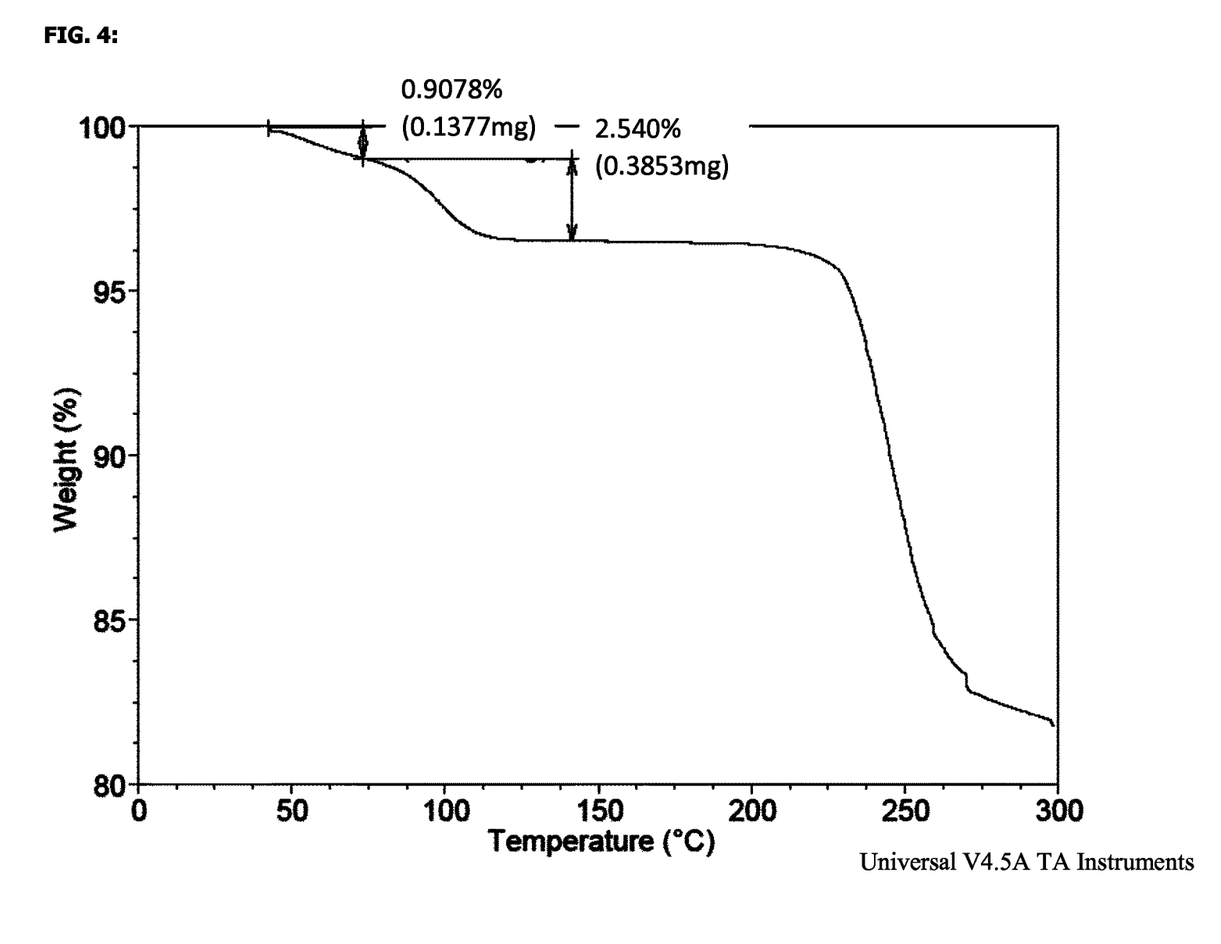
FIG. 4 shows a thermogravimetric analysis thermogram of the compound of the invention.

In a further embodiment, there is provided a crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, which has a FT Raman spectrum substantially as shown in FIG. 3.

In a further embodiment, there is provided a crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate characterised by an FT-Raman spectrum obtained under the conditions described hereinabove, comprising peaks at 805, 1017, 1060, 1117, 1211, 1253, 1264, 1282, 1295, 1331, 1363, 1413, 1459, 1514, 1575, 1631, 2932, 2966 and 3062 cm$^{-1}$, wherein the margin of error in each band position is approximately ±1 cm$^{-1}$.

In another further embodiment, there is provided a crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)

amino)-3-hydroxybutanoate edisylate, characterised by an FT-Raman spectrum obtained under the conditions described hereinabove, comprising at least fifteen peaks selected from a group consisting of 805, 1017, 1060, 1117, 1211, 1253, 1264, 1282, 1295, 1331, 1363, 1413, 1459, 1514, 1575, 1631, 2932, 2966 and 3062 cm$^{-1}$, wherein the margin of error in each band position is approximately ±1 cm$^{-1}$.

In another further embodiment, there is provided a crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, characterised by an FT-Raman spectrum obtained under the conditions described hereinabove, comprising at least twelve peaks selected from a group consisting of 805, 1017, 1060, 1117, 1211, 1253, 1264, 1282, 1295, 1331, 1363, 1413, 1459, 1514, 1575, 1631, 2932, 2966 and 3062 cm$^{-1}$, wherein the margin of error in each band position is approximately ±1 cm$^{-1}$.

In another further embodiment, there is provided a crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, characterised by an FT-Raman spectrum obtained under the conditions described hereinabove, comprising at least ten peaks selected from a group consisting of 805, 1017, 1060, 1117, 1211, 1253, 1264, 1282, 1295, 1331, 1363, 1413, 1459, 1514, 1575, 1631, 2932, 2966 and 3062 cm$^{-1}$, wherein the margin of error in each band position is approximately ±1 cm$^{-1}$.

In another further embodiment, there is provided a crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, characterised by an FT-Raman spectrum obtained under the conditions described hereinabove, comprising at least eight peaks selected from a group consisting of 805, 1017, 1060, 1117, 1211, 1253, 1264, 1282, 1295, 1331, 1363, 1413, 1459, 1514, 1575, 1631, 2932, 2966 and 3062 cm$^{-1}$, wherein the margin of error in each band position is approximately ±1 cm$^{-1}$.

In a still further embodiment, there is provided a crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate which, as a person having ordinary skill in the art will understand, is characterized by any combination of the analytical data characterizing the aforementioned embodiments. For example, in one embodiment, the crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate has an X-ray powder diffraction pattern substantially as shown in FIG. 1 and a DSC thermogram substantially as shown in FIG. 2 and an FT Raman spectrum substantially as shown in FIG. 3. In another embodiment, the crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate has an X-ray powder diffraction pattern substantially as shown in FIG. 1 and a DSC thermogram substantially as shown in FIG. 2.

In another embodiment, the crystalline hydrate form of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate has an X-ray powder diffraction pattern substantially as shown in FIG. 1 and an FT Raman spectrum substantially as shown in FIG. 3.

It is well known and understood to those skilled in the art that the apparatus employed, humidity, temperature, orientation of the powder crystals, and other parameters involved in obtaining an X-ray powder diffraction (XRPD) pattern may cause some variability in the appearance, intensities, and positions of the lines in the diffraction pattern. An X-ray powder diffraction pattern that is "substantially as shown in FIG. 1" provided herein is an XRPD pattern that would be considered by one skilled in the art to represent a compound possessing the same crystal form as the compound that provided the XRPD pattern of FIG. 1. That is, the XRPD pattern may be identical to that of FIG. 1, or more likely it may be somewhat different. Such an XRPD pattern may not necessarily show each of the lines of any one of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay an XRPD pattern of a sample of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, with FIG. 1 and, using expertise and knowledge in the art, readily determine whether the XRPD pattern of the sample is substantially as shown in FIG. 1. If the XRPD pattern is substantially as shown in FIG. 1, the sample form can be readily and accurately identified as having the same form as the compound of the invention.

Further, it is also well known and understood to those skilled in the art that the apparatus employed, humidity, temperature, orientation of the powder crystals, and other parameters involved in obtaining a Raman spectrum may cause some variability in the appearance, intensities, and positions of the peaks in the spectrum. A Raman spectrum that is "substantially as shown in FIG. 3" provided herein is a Raman spectrum that would be considered by one skilled in the art to represent a compound possessing the same crystal form as the compound that provided the Raman spectrum of FIG. 3. That is, the Raman spectrum may be identical to that of FIG. 3, or more likely it may be somewhat different. Such a Raman spectrum may not necessarily show each of the peaks of any one of the spectra presented herein, and/or may show a slight change in appearance, intensity, or a shift in position of said peaks resulting from differences in the conditions involved in obtaining the data. A person skilled in the art is capable of determining if a sample of a crystalline compound has the same form as, or a different form from, a form disclosed herein by comparison of their Raman spectra. For example, one skilled in the art can overlay a Raman spectrum of a sample of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, with FIG. 3 and, using expertise and knowledge in the art, readily determine whether the Raman spectrum of the sample is substantially as shown in FIG. 3. If the XRPD pattern is substantially as shown in FIG. 3, the sample form can be readily and accurately identified as having the same form as the compound of the invention. The present invention relates to a hydrate, for example a monohydrate, of the edisylate salt of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate. In a preferred embodiment, the hydrate is in crystalline form. Amorphous forms of the hydrate (e.g. amorphous monohydrate) also form part of the present invention. For a crystalline hydrated form, the degree of crystallinity is greater than about 60%, 70%, 80%, 90%, 95%, 96%, 97%, 98%, or 99%. In one embodiment, the degree of crystallinity is greater than 99%.

A crystalline hydrate of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate disclosed herein may show an improved profile over known BET inhibitors in that it may possess, for example, one or more of the following properties:
(i) potent BET inhibitory activity;
(ii) selectivity over other known bromodomain containing proteins outside of the BET family of proteins;
(iii) selectivity for a particular BET family member over one or more other BET family members;
(iv) selectivity for one Binding Domain (i.e. BD1 over BD2) for any given BET family member;
(v) improved developability (e.g. desirable solubility profile, pharmacokinetics and pharmacodynamics); or
(vi) a reduced side-effect profile.

The present invention also includes all suitable isotopic variations of the compounds of the invention. An isotopic variation of a compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, fluorine and chlorine such as $^{2}H$, $^{3}H$, $^{13}C$, $^{14}C$, $^{15}N$, $^{17}O$, $^{18}O$, $^{18}F$ and $^{36}Cl$, respectively. Certain isotopic variations of the compound of formula (I) or a salt thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures such as by the illustrative methods or by the preparations described in the Examples hereafter using appropriate isotopic variations of suitable reagents.

STATEMENT OF USE

The compound of formula (I), the edisylate salt thereof (the compound of formula (II)) and a crystalline hydrate thereof which is disclosed herein are known to be BET inhibitors and thus may have therapeutic utility in the treatment of a variety of diseases or conditions related to systemic or tissue inflammation, inflammatory responses to infection or hypoxia, cellular activation and proliferation, lipid metabolism, fibrosis and in the prevention and treatment of viral infections. In one embodiment, a compound of the invention is capable of inhibiting the binding of each BET family bromodomain containing protein (e.g. BRD2, BRD3, BRD4 and BRDT) to acetylated lysine residues. In a further embodiment, a compound of the invention is capable of inhibiting the binding of BRD4 to its cognate acetylated lysine residue.

BET inhibitors may be useful in the treatment of a wide variety of acute or chronic autoimmune and/or inflammatory conditions such as rheumatoid arthritis, osteoarthritis, acute gout, psoriasis, systemic lupus erythematosus, pulmonary arterial hypertension (PAH), multiple sclerosis, inflammatory bowel disease (Crohn's disease and ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, depression, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macular edema, age-related macular dystrophy, hepatitis, pancreatitis, primary biliary cirrhosis, sclerosing cholangitis, Addison's disease, hypophysitis, thyroiditis, type I diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's arteritis, pyoderma gangrenosum, vasculitis with organ involvement and acute rejection of transplanted organs. The use of BET inhibitors for the treatment of rheumatoid arthritis is of particular interest.

In one embodiment, the acute or chronic autoimmune and/or inflammatory condition is a disorder of lipid metabolism via the regulation of APO-A1 such as hypercholesterolemia, atherosclerosis and Alzheimer's disease.

In another embodiment, the acute or chronic autoimmune and/or inflammatory condition is a respiratory disorder such as asthma or chronic obstructive airways disease.

In another embodiment, the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease and ulcerative colitis).

In another embodiment, the acute or chronic autoimmune and/or inflammatory condition is multiple sclerosis.

In a further embodiment, the acute or chronic autoimmune and/or inflammatory condition is type I diabetes.

BET inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment, the disease or condition which involves an inflammatory response to an infection with bacteria, a virus, fungi, a parasite or their toxins is acute sepsis.

BET inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardiopulmonary bypass procedures, pulmonary, renal, hepatic, gastro-intestinal or peripheral limb embolism.

BET inhibitors may be useful in the treatment of fibrotic conditions such as idiopathic pulmonary fibrosis, renal fibrosis, post-operative stricture, keloid scar formation, scleroderma (including morphea), cardiac fibrosis and cystic fibrosis.

BET inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox and smallpox and African swine fever virus. In one embodiment, the viral infection is a HPV infection of skin or cervical epithelia. In another embodiment, the viral infection is a latent HIV infection.

BET inhibitors may be useful in the treatment of cancer, including hematological (such as leukaemia, lymphoma and multiple myeloma), epithelial including lung, breast and colon carcinomas, midline carcinomas, mesenchymal, hepatic, renal and neurological tumours.

BET inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharyngeal cancer, buccal cancer, cancer of the mouth, GIST (gastrointestinal stromal tumor), NUT-midline carcinoma and testicular cancer.

In one embodiment, the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment, the cancer is NUT-midline carcinoma. In another embodiment, the cancer is multiple myeloma. In another embodiment, the cancer is a lung cancer such as small cell lung cancer (SCLC). In another embodiment, the cancer is a neuroblastoma. In another embodiment, the cancer is Burkitt's lymphoma. In another embodiment, the cancer is cervical cancer. In another embodiment, the cancer is esophageal cancer. In another embodiment, the cancer is ovarian cancer. In another embodiment, the cancer is breast cancer. In another embodiment, the cancer is colorectal cancer. In another embodiment, the cancer is prostate cancer. In another embodiment, the cancer is castration-resistant prostate cancer.

In one embodiment, the disease or condition for which a BET inhibitor is indicated is selected from diseases associated with systemic inflammatory response syndrome, such as sepsis, burns, pancreatitis, major trauma, haemorrhage and ischaemia. In this embodiment, the BET inhibitor would be administered at the point of diagnosis to reduce the incidence of SIRS, the onset of shock, multi-organ dysfunction syndrome, which includes the onset of acute lung injury, ARDS, acute renal, hepatic, cardiac or gastro-intestinal injury and mortality. In another embodiment, the BET inhibitor would be administered prior to surgical or other procedures associated with a high risk of sepsis, haemorrhage, extensive tissue damage, SIRS or MODS (multiple organ dysfunction syndrome). In a particular embodiment, the disease or condition for which a BET inhibitor is indicated is sepsis, sepsis syndrome, septic shock and endotoxemia. In another embodiment, the BET inhibitor is indicated for the treatment of acute or chronic pancreatitis. In another embodiment, the BET inhibitor is indicated for the treatment of burns.

In a further aspect, the present invention provides a compound of the invention for use in therapy.

In a further aspect, the present invention provides a compound of the invention for use in the treatment of diseases or conditions for which a BET inhibitor is indicated.

In a further aspect, the present invention also provides a compound of the invention for use in the treatment of autoimmune and/or inflammatory diseases, and cancer.

In a further aspect, the present invention provides a compound of the invention for use in the treatment of rheumatoid arthritis.

In a further aspect, the present invention provides a compound of the invention for use in the treatment of osteoarthritis.

In a further aspect, the present invention is directed to a method of treatment of an autoimmune and/or inflammatory disease, which comprises administering to a subject in need thereof, a therapeutically effective amount of a compound of the invention. In one embodiment, the subject is a human subject.

In yet a further aspect, the present invention is directed to a method of treating rheumatoid arthritis, which comprises administering to a subject in need thereof, a therapeutically effective amount of a compound of the invention.

In yet a further aspect, the present invention is directed to a method of treating osteoarthritis, which comprises administering to a subject in need thereof, a therapeutically effective amount of a compound of the invention.

In a further aspect, the present invention is directed to the use of a compound of the invention in the manufacture of a medicament for use in the treatment of an autoimmune and/or inflammatory disease.

In a further aspect, the present invention is directed to the use of a compound of the invention in the manufacture of a medicament for use in the treatment of rheumatoid arthritis.

In a further aspect, the present invention is directed to the use of a compound of the invention in the manufacture of a medicament for use in the treatment of osteoarthritis.

Pharmaceutical Compositions/Routes of Administration/Dosages

While it is possible that for use in therapy, a compound of the invention may be administered as the raw chemical, it is common to present the active ingredient as a pharmaceutical composition.

In a further aspect, there is provided a pharmaceutical composition comprising a compound of the invention and one or more pharmaceutically acceptable excipients.

The excipient(s) must be pharmaceutically acceptable and be compatible with the other ingredients of the composition. In accordance with another aspect of the invention there is also provided a process for the preparation of a pharmaceutical composition including admixing a compound of the invention with one or more pharmaceutically acceptable excipients. The pharmaceutical composition can be used in the treatment of any of the diseases described herein.

Since a compound of the invention is intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the excipient(s).

In one aspect, the pharmaceutical composition is adapted for oral administration. Pharmaceutical compositions adapted for oral administration may be presented as discrete units such as tablets or capsules; powders or granules; solutions or suspensions in aqueous or non-aqueous liquids; edible foams or whips; or oil-in-water liquid emulsions or water-in-oil liquid emulsions.

Powders suitable for incorporating into tablets or capsules may be prepared by reducing a compound of the invention to a suitable fine size (e.g. by micronisation) and mixing with a similarly prepared pharmaceutical excipient such as an edible carbohydrate, for example, starch or mannitol. Flavoring, preservative, dispersing and coloring agents, for example, may also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. A compound of the invention can also be combined with a free flowing inert excipient and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

Pharmaceutical compositions for nasal or inhaled administration may conveniently be formulated as aerosols, solutions, suspensions, gels or dry powders. For compositions suitable for and/or adapted for inhaled administration, it is preferred that a compound of the invention is in a particle-size-reduced form e.g. obtained by micronisation. The preferable particle size of the size-reduced (e.g. micronised) compound is defined by a D50 value of about 0.5 to about 10 microns (for example as measured using laser diffraction).

The pharmaceutical composition for inhaled administration may be a dry powder composition or an aerosol formulation, comprising a solution or fine suspension of the active substance in a pharmaceutically acceptable aqueous or non-aqueous solvent. Dry powder compositions can comprise a powder base such as lactose, glucose, trehalose, mannitol or starch, a compound of the invention (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and a compound of the invention.

In one embodiment, a dry powder composition suitable for inhaled administration may be incorporated into a plurality of sealed dose containers provided on medicament pack(s) mounted inside a suitable inhalation device. The containers may be rupturable, peelable or otherwise openable one-at-a-time and the doses of the dry powder composition administered by inhalation on a mouthpiece of the inhalation device, as known in the art. The medicament pack may take a number of different forms, for instance a diskshape or an elongate strip. Representative inhalation devices are the DISKHALER™ inhaler device, the DISKUS™ inhalation device, and the ELLIPTA™ inhalation device, marketed by GlaxoSmithKline. The DISKUS™ inhalation device is, for example, described in GB 2242134A, and the ELLIPTA™ inhalation device is, for example, described in WO 03/061743 A1 WO 2007/012871 A1 and/or WO2007/068896.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

A therapeutically effective amount of a compound of the invention will depend upon a number of factors including, for example, the age and weight of the subject, the precise condition requiring treatment and its severity, the nature of the formulation, and the route of administration, and will ultimately be at the discretion of the attendant physician or veterinarian. In the pharmaceutical composition, each dosage unit may contain from 0.01 to 1000 mg, more preferably 0.5 to 100 mg, of a compound of formula (I) or a pharmaceutically acceptable salt thereof, calculated as the free base.

A compound of the invention may be employed alone or in combination with other therapeutic agents. Combination therapies according to the present invention thus comprise the administration of at least one compound of the invention and the use of at least one other therapeutically active agent. A compound of the invention and the other therapeutically active agent(s) may be administered together in a single pharmaceutical composition or separately and, when administered separately this may occur simultaneously or sequentially in any order.

In a further aspect, there is provided a pharmaceutical composition comprising a compound of the invention together with one or more other therapeutically active agents, and optionally one or more pharmaceutically acceptable carriers, diluents or excipients.

It will be clear to a person skilled in the art that, where appropriate, the other therapeutic ingredient(s) may be used in the form of salts, for example as alkali metal or amine salts or as acid addition salts, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with one or more pharmaceutically acceptable excipients represent a further aspect of the invention.

EXAMPLE PREPARATION

Abbreviations

DCM Dichloromethane
DIPEA diisopropylethylamine
DMF N,N-dimethylformamide
DMSO Dimethylsulfoxide
g Grammes
h Hour(s)
EtOAc Ethyl acetate
$Et_3N$ Triethylamine
HPLC High-performance liquid chromatography
L Litre
LCMS Liquid chromatography-mass spectrometry
min Minutes
mg Milligrammes
MHz Megahertz
mL Millilitre
mM Millimolar
nm Nanometre
ppm Parts per million
RT Room temperature
rpm revolutions per minute
$t_{RET}$ Retention time
m Micrometre Experimental Details LCMS
System A
Column: 50 mm×2.1 mm ID, 1.7 m Acquity UPLC CSH $C_{18}$
Flow Rate: 1 mL/min.
Temp: 40° C.

UV detection range: 210 to 350 nm
Mass spectrum: Recorded on a mass spectrometer using alternative-scan positive and
negative mode electrospray ionisation
The solvents employed were:
A=10 mM ammonium bicarbonate in water adjusted to pH10 with ammonia solution.
B=Acetonitrile.
Gradient:

| Time (min.) | A % | B % |
|---|---|---|
| 0 | 97 | 3 |
| 1.5 | 5 | 95 |
| 1.9 | 5 | 95 |
| 2.0 | 97 | 3 |

¹H NMR

The ¹H NMR spectrum was recorded in DMSO-$d_6$ on a Bruker AV-400 400 MHz spectrometer with cryo-probe, and referenced to TMS at 0.00 ppm.

Example 1: Preparation of (2S,3R)-Isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (Compound of formula (I))

(I)

(3-Nitro-4-(((tetrahydro-2H-pyran-4-yl)methyl)amino)phenyl)methanol (4-fluoro-3-nitrophenyl)methanol (2.4 g, 14.02 mmol) and (tetrahydro-2H-pyran-4-yl)methanamine (2.423 g, 21.04 mmol) were suspended in water (30 ml) and potassium carbonate (2.52 g, 18.23 mmol) was added, then the mixture was stirred at 80° C. for 24 h, then allowed to cool while stirring. The resulting mixture was extracted with EtOAc (50 mL) and the organic layer washed with water (50 ml), dried and evaporated in vacuo to give the title compound (3.60 g, 13.52 mmol, 96% yield) as a dark yellow solid. LCMS (System A): $t_{RET}$=0.82 min; MH⁺ 267. The title compound was used in the next step without purification.

(3-Amino-4-(((tetrahydro-2H-pyran-4-yl)methyl)amino)phenyl)methanol (3-Nitro-4-(((tetrahydro-2H-pyran-4-yl)methyl)amino)phenyl)methanol (48 g, 180 mmol) was dissolved in ethanol (400 mL) and hydrogenated over Pd/C 5% by weight (3 g, 28.2 mmol) at atmospheric pressure for 18 h, then the mixture was filtered through Celite under nitrogen, and the filtrate evaporated in vacuo to give the title compound (50 g, 212 mmol, 117% yield) as a dark brown oil. LCMS (System A): $t_{RET}$=0.62 min; MH⁺ 237. Product was carried through to the next step without further purification.

5-(5-(Hydroxymethyl)-1-((tetrahydro-2H-pyran-4-yl)methyl)-1H-benzo[d]imidazol-2-yl)-1,3-dimethyl-pyridin-2-(1H)-one (3-Amino-4-(((tetrahydro-2H-pyran-4-yl)methyl)amino)phenyl)methanol (50 g, 190 mmol) was suspended in water (500 mL) and 1,5-dimethyl-6-oxo-1,6-dihydropyridine-3-carbaldehyde (31.7 g, 209 mmol) and cetylpyridinium bromide (14.64 g, 38.1 mmol) were added, then the mixture was stirred vigorously overnight. The mixture was extracted with DCM (3×300 mL) and the combined organics were washed with brine (500 mL), then dried and evaporated to give a dark brown solid. This was suspended in EtOAc (500 mL) and heated to reflux for 2 h, then cooled and the product collected by filtration. The crude was resuspended in EtOAc (500 ml) and heated to reflux again, then cooled in an ice bath and the product collected by filtration and washed with ether (300 ml) to give a brown solid (64 g). LCMS showed clean product, but the NMR spectrum shows the presence of 0.2 eq of the cetylpyridinium salt remaining in the product. Carried through to the next step without purification. The title compound was 90% Wt purity. LCMS (System A): $t_{RET}$=0.66 min; MH⁺ 368.

(2S,3R)-isopropyl 2-amino-3-hydroxybutanoate, hydrochloride

AcCl (96 mL, 1343 mmol) was added dropwise to 2-propanol (500 mL, 6490 mmol) and the mixture was then stirred for 20 min before addition of (2S,3R)-2-amino-3-hydroxybutanoic acid (40 g, 336 mmol). The resulting suspension was heated to reflux overnight, then cooled and evaporated in vacuo to give a colourless oil. This was triturated with ether (300 mL) and the product collected by filtration to give the title compound as a colourless solid.
¹H NMR (400 MHz, DMSO-$d_6$) δ 8.49 (br. s., 3H), 5.66 (br. s., 1H), 4.99 (td, J=6.24, 12.47 Hz, 1H), 4.09 (br. s., 1H), 3.80 (d, J=4.16 Hz, 1H), 1.17-1.29 (m, 9H)

2-(1,5-dimethyl-6-oxo-1,6-dihydropyridin-3-yl)-1-((tetrahydro-2H-pyran-4-yl)methyl)-1H-benzo[d]imidazole-5-carbaldehyde 5-(5-(Hydroxymethyl)-1-((tetrahydro-2H-pyran-4-yl)methyl)-1H-benzo[d]imidazol-2-yl)-1,3-dimethylpyridin-2(1H)-one (64 g, 122 mmol) was dissolved in DCM (600 mL) and manganese dioxide (42.4 g, 488 mmol) was added, then the mixture was heated at reflux for 18 h. LCMS showed complete conversion, and the mixture was filtered and the solid washed with DCM. The filtrate was evaporated in vacuo to give a brown gum, which was dissolved in DCM (100 mL) and loaded onto a 340 g silica column, then eluted with 0-50% EtOH/EtOAc and product-containing fractions were evaporated in vacuo to give a brown solid. This was triturated with ether (200 mL) and the solid collected by filtration, then suspended in EtOAc (300 mL) and heated to reflux for 1 h, then cooled in an ice bath and the product collected by filtration to give 2-(1,5-dimethyl-6-oxo-1,6-dihydropyridin-3-yl)-1-((tetrahydro-2H-pyran-4-yl)methyl)-1H-benzo[d]imidazole-5-carbaldehyde (42.5 g, 116 mmol, 95% yield) as a sand-coloured solid. LCMS (System A): $t_{RET}$=0.74 min; MH+ 366. The filtrate was evaporated in vacuo and the residue triturated in EtOAc (50 mL) at reflux for 30 min, then cooled and filtered to give an additional portion of the product (3 g) as a beige solid, NMR consistent with the desired aldehyde. The title compound was 80% Wt purity.

(2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate 2-(1,5-dimethyl-6-oxo-1,6-dihydropyridin-3-yl)-1-((tetrahydro-2H-pyran-4-yl)methyl)-1H-benzo[d]imidazole-5-carbaldehyde (42 g, 115 mmol) and (2S,3R)-isopropyl 2-amino-3-hydroxybutanoate hydrochloride (34.1 g, 172 mmol) were dissolved in DCM (500 mL), then Et$_3$N (48.1 mL, 345 mmol) was added, followed by sodium triacetoxyborohydride (73.1 g, 345 mmol) and the mixture was stirred at room temperature for 24 h. The mixture was added to 1.5 litres of saturated sodium bicarbonate solution in a 5 litre conical flask and stirred vigorously for 1 h, then the organic layer was separated, the aqueous extracted with DCM (500 mL) and the combined organics washed with water (500 mL) and brine (500 mL), dried over sodium sulphate and evaporated in vacuo to give a brown foam. The crude product was dissolved in DCM (200 mL) and loaded onto a 750 g silica column, then eluted with 0-30% EtOH/EtOAc and clean product-containing fractions were evaporated in vacuo to give the title compound (51 g, 100 mmol, 87% yield) as a beige foam. LCMS (System A): $t_{RET}$=0.86 min; MH+ 511.

$^1$H NMR (d6-DMSO): δ 1.06-1.26 (m, 13H), 1.90-2.02 (m, 1H), 2.11 (s, 3H), 2.20-2.41 (m, 1H), 3.00 (d, J=4.9 Hz, 1H), 3.05-3.16 (m, 2H), 3.56 (s, 3H), 3.66 (d, J=1.32 Hz, 1H), 3.76-3.86 (m, 1H), 3.90 (d, J=13.2 Hz, 1H), 4.26 (d, J=7.3 Hz, 2H), 4.67 (d, J=5.4 Hz, 1H), 4.93 (sept, J=6.2 Hz, 1H), 7.22 (dd, J=8.3, 1.2 Hz, 1H), 7.53 (s, 1H), 7.61 (d, J=8.3 Hz, 1H), 7.73 (dd, J=2.3, 1.1 Hz, 1H), 8.12 (d, J=2.2 Hz, 1H).

Example 2: Preparation of the Edisylate Salt of (2S,3R)-Isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate To a carousel tube was added (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (For a preparation see Example 1, 100 mg, 0.196 mmol) and isopropanol (1.35 mL). The stirred mixture was heated to 40° C. and a solution of ethane-1,2-disulfonic acid (44.7 mg, 0.235 mmol) in isopropanol (557 µL) was added. The mixture was stirred at 40° C. for 15 hr. After this time, solid had formed. The reaction was removed from the carousel, cooled directly to 24° C. and stirred for 6 h. After this time, the suspension was filtered and dried under vacuum for 5 min. The solid, transferred into a vial was further dried in the vacuum oven at 40° C. for 3 days to yield the title compound (91 mg, 66.3% yield) as a white crystalline solid. $^1$H NMR (400 MHz, DMSO-d$_6$) δ ppm 9.61 (1H, br. s.), 9.29 (1H, br. s.), 8.35 (1H, br. s.), 8.02 (1H, d, J=8.6 Hz), 7.92 (1H, s), 7.82-7.75 (1H, m), 7.58 (1H, d, J=8.6 Hz), 4.94 (1H, spt, J=6.2 Hz), 4.46-4.34 (4H, m), 4.05 (1H, quin, J=6.4 Hz), 3.77-3.69 (2H, m), 3.66 (1H, br. s.), 3.59 (3H, s), 3.17-3.08 (2H, m), 2.66 (4H, s), 2.13 (3H, s), 2.06-1.93 (1H, m), 1.31-1.16 (13H, m). LCMS (System A): $t_{RET}$=0.88 min; MH+ 511.

Example 3: Alternative Preparation of the Edisylate Salt (2S,3R)-Isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl) amino)-3-hydroxybutanoate (Compound of formula (II))

To an EasyMax 400 mL reactor was added (2S,3R)-Isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (for an example preparation see Example 1)(10 g, 19.58 mmol) and Isopropanol (135 mL). In a separate flask was prepared a solution of ethane-1,2-disulfonic acid (4.47 g, 23.50 mmol) in Isopropanol (28 mL) warmed at 40° C. and filtered.

To the solution of (2S,3R)-Isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl) amino)-3-hydroxybutanoate, stirred at 250 rpm was added 40% of the ethane-1,2-disulfonic acid solution (11.2 mL). A seed of the edisylate salt (2S,3R)-Isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl) amino)-3-hydroxybutanoate (see, for example, Example 2 above) (131 mg) was added and the mixture was stirred at 40° C. for 1.5 h. After this time, the remaining 60% of the ethane-1,2-disulfonic acid solution (16.8 mL) was added dropwise over 6 h. On complete addition of ethane-1,2-disulfonic acid solution the mixture was slowly cooled to 20° C. over 3.5 h and stirred for a further 11 h at RT. The resulting suspension was filtered with filter cup and paper filter, with the filtrate running clear. The filter cake was washed with IPA (2×20 mL and 10 mL) and further dried under with vacuum to yield the wet filter cake (24.06 g). The solids were collected and dried in a vacuum oven (44° C.) for 22 h to yield the title compound (11.337 g, 16.02 mmol, 82% yield) as a white crystalline solid. LCMS (System A): $t_{RET}$=0.88 min; MH+ 511.

Example 4: Preparation of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate 1,2-ethanedisulphonate hydrate salt

A solution of ethane 1,2-disulfonic acid (467.4 mg) in deionised water (175 µL) was added to a solution of amorphous (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate (for an example preparation see Example 1) (1.0 g) in acetone (8 mL), in a Wheaton vial with a stirrer bar at RT (26° C.). The vial containing the ethane 1-2-disulfonic acid was rinsed with deionised water (175 µL). The mixture was heated to 50° C. then stirred for 30 minutes at 50° C. The reaction mixture was cooled from 50° C. to RT over an hour, and then re-heated from RT to 50° C. The temperature was maintained at 50° C. for 30 minutes, and then cooled to 26° C. The suspension was stirred for 14.5 hours at 26° C. The solid was isolated by filtration and deliquored under vacuum for 10 minutes to give the title compound as a white crystalline solid (824 mg).

Example 5: Alternative Preparation of (2S,3R)-Isopropyl 2-(((2-(1,5-Dimethyl-6-Oxo-1,6-dihydropyridin-3-yl)-1-((tetrahydro-2H-pyran-4-yl)methyl)-1H-benzo[d]imidazol-5-yl)methyl)amino)-3-hydroxybutanoate, 1,2-ethanedisulphonic acid hydrate salt To a stirred suspension of crystalline (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate 1,2-ethanedisulphonate (for an example preparation see Example 2 or 3) (26 mg), in 7.3% v/v aqueous propan-2-ol (0.1 mL) was added some crystalline seeds of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)

phore. A small molecule, high affinity binder of the bromodomains BRD2, BRD3, BRD4 and BRDT has been labeled with Alexa Fluor647 (Reference Compound X) and this acts as the acceptor in the FRET pair.

Reference Compound X: 4-((Z)-3-(6-((5-(2-((4S)-6-(4-chlorophenyl)-8-methoxy-1-methyl-4H-benzo[f][1,2,4]triazolo[4,3-a][1,4]diazepin-4-yl)acetamido)pentyl)amino)-6-oxohexyl)-2-((2E,4E)-5-(3,3-dimethyl-5-sulfo-1-(4-sulfobutyl)-3H-indol-1-ium-2-yl)penta-2,4-dien-1-ylidene)-3-methyl-5-sulfoindolin-1-yl)butane-1-sulphonate)

amino)-3-hydroxybutanoate 1,2-ethanedisulphonate hydrate (for an example preparation see Example 4). Conversion of the anhydrate to the hydrate was observed within 5 minutes.

BIOLOGICAL DATA

Time Resolved Fluorescence Resonance Energy Transfer (TR-FRET) Assay

Binding was assessed using a time resolved fluorescent resonance energy transfer binding assay. This utilises a 6 His purification tag at the N-terminal of the proteins as an epitope for an anti-6 His antibody labeled with Europium chelate (PerkinElmer AD0111) allowing binding of the Europium to the proteins which acts as the donor fluoro- To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO2011/054848A1, 1.7 mg, 3.53 μmol) in DMF (40 μL) was added a solution of AlexaFluor647-ONSu (2.16 mg, 1.966 μmol) also in DMF (100 μL). The mixture was basified with DIPEA (1 μL, 5.73 μmol) and agitated overnight on a vortex mixer. The reaction mixture was evaporated to dryness. The solid was dissolved in acetonitrile/water/acetic acid (5/4/1, <1 mL) filtered and was applied to a Phenomenex Jupiter C18 preparative column and eluted with the following gradient (A=0.1% trifluoroacetic acid in water, B=0.1% TFA/90% acetonitrile/10% water): Flow rate=10 ml/min., AU=20/10 (214 nm):

5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B.

Fractions F1.25/26&27 were combined and evaporated to dryness. Transferred with DMF, evaporated to dryness, triturated with dry ether and the blue solid dried overnight at <0.2 mbar: 1.54 mg.

Analytical HPLC (Sphersisorb ODS2, 1 to 35% B over 60 min): MSM10520-1: $[M+H]^+$ (obs): 661.8/– corresponding with M-29. This equates to $[(M+2H)/2]^+$ for a calculated mass of 1320.984 which is M-29. This is a standard occurrence with the Alexa Fluor 647 dye and represents a theoretical loss of two methylene groups under the conditions of the mass spectrometer.

Assay Principle:

In the absence of a competing compound, excitation of the Europium causes the donor to emit at 32618 nm which excites the Alexa labelled bromodomain binding compound leading to an increased energy transfer that is measurable at 32647 nM. In the presence of a sufficient concentration of a compound that can bind these proteins, the interaction is disrupted leading to a quantifiable drop in fluorescent resonance energy transfer.

The binding of compounds of the invention to Bromodomains BRD2, BRD3, BRD4 and BRDT was assessed using mutated proteins to detect differential binding to either Binding Domain 1 (BD1) or Binding Domain 2 (BD2) on the bromodomain. These single residue mutations in the acetyl lysine binding pocket greatly lower the affinity of the fluoroligand (Reference Compound X) for the mutated domain (>1000 fold selective for the non-mutated domain). Therefore in the final assay conditions, binding of the fluoroligand to the mutated domain cannot be detected and subsequently the assay is suitable to determine the binding of compounds to the single non-mutated bromodomain.

Protein Production:

Recombinant Human Bromodomains [(BRD2 (1-473) (Y113A) and (Y386A), BRD3 (1-435) (Y73A) and (Y348A) BRD4 (1-477) (Y97A) and (Y390A) and BRDT (1-397) (Y66A) and (Y309A)] were expressed in *E. coli* cells (in pET15b vector for BRD2/3/4 and in pET28a vector for BRDT) with a 6-His tag at the N-terminal. The His-tagged Bromodomain pellet was resuspended in 50 mM HEPES (pH7.5), 300 mM NaCl, 10 mM imidazole & 1 µl/ml protease inhibitor cocktail and extracted from the *E. coli* cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at –80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3, 4 and T, BD1+BD2 Mutant Assays:

All assay components were dissolved in buffer composition of 50 mM HEPES pH7.4, 50 mM NaCl, 5% Glycerol, 1 mM DTT and 1 mM CHAPS. The final concentration of bromodomain proteins were 10 nM and the Alexa Fluor647 ligand was at Kd. These components were premixed and 5 µL of this reaction mixture was added to all wells containing 50 nl of various concentrations of test compound or DMSO vehicle (0.5% DMSO final) in Greiner 384 well black low volume microtitre plates and incubated in dark for 30 minutes at rt. 5 µL of detection mixture containing 1.5 nM final concentration anti-6His Europium chelate was added to all wells and a further dark incubation of at least 30 minutes was performed. Plates were then read on the Envision platereader, (•ex=317 nm, donor •em=615 nm; acceptor •em=665 nm; Dichroic LANCE dual). Time resolved fluorescent intensity measurements were made at both emission wavelengths and the ratio of acceptor/donor was calculated and used for data analysis. All data was normalized to the mean of 16 high (inhibitor control—Example 11 of WO 2011/054846A1) and 16 low (DMSO) control wells on each plate. A four parameter curve fit of the following form was then applied:

$$y=a+((b-a)/(1+(10\char`^x/10\char`^c)\char`^d))$$

Where 'a' is the minimum, 'b' is the Hill slope, 'c' is the $pIC_{50}$ and 'd' is the maximum.

Results:

Example 1 was found to have a mean $pIC_{50}$ of 7.3 in the BRD4 BD1 assay and a mean $pIC_{50}$ of 6.8 in the BRD4 BD2 assay. The edisylate salt of Example 1 was found to have a mean $pIC_{50}$ of 7.3 in the BRD4 BD1 assay and a mean $pIC_{50}$ of 6.6 in the BRD4 BD2 assay.

Measurement of LPS Induced MCP-1 Production from Human Whole Blood

Activation of monocytic cells by agonists of toll-like receptors such as bacterial lipopolysaccharide (LPS) results in production of key inflammatory mediators including MCP-1. Such pathways are widely considered to be central to the pathophysiology of a range of auto-immune and inflammatory disorders. Blood is collected in a tube containing Sodium heparin (Leo Pharmaceuticals) (10 units of heparin/mL of blood). 96-well compound plates containing 1 µL test sample in 100% DMSO were prepared (two replicates on account of donor variability). 130 µL of whole blood was dispensed into each well of the 96-well compound plates and incubated for 30 min at 37° C., 5% $CO_2$. 10 µL of lipopolysaccharide (from *Salmonella typhosa*; L6386) made up in PBS (200 ng/mL final assay concentration) was added to each well of the compound plates. The plates were then placed in the humidified primary cell incubator for 18-24 hours at 37° C., 5% $CO_2$. 140 µL of PBS was added to all wells of the compound plates containing blood. The plates were then sealed and centrifuged for 10 mins at 2500 rpm. 25 µL of cell supernatant was placed in a 96-well MSD plate pre-coated with human MCP-1 capture antibody. The plates were sealed and placed on a shaker at 600 rpm for 1 hour (rt). 25 µL of Anti-human MCP-1 antibody labelled with MSD SULFO-TAG™ reagent is added to each well of the MSD plate (stock 50× was diluted 1:50 with Diluent 100, final assay concentration is 1 µg/mL). The plates were then re-sealed and shaken for another hour before washing with PBS. 150 µL of 2×MSD Read Buffer T (stock 4×MSD Read Buffer T was diluted 50:50 with de-ionised water) was then added to each well and the plates read on the MSD Sector Imager 6000. Concentration response curves for each compound were generated from the data and an $pIC_{50}$ value was calculated.

Results:

Example 1 had a mean $pIC_{50}$ of 7.6. The edisylate salt of Example 1 had a mean $pIC_{50}$ of 7.5.

These data demonstrate that bromodomain inhibitors tested in the above whole blood assay inhibited the production of key inflammatory mediator MCP-1.

Hydrolysis by hCES-1

Hydrolysis of ESM-containing BET inhibitors by carboxylesterase 1 (CES1) is one aspect of delivering a targeted molecule. Rates of hydrolysis of certain compounds of the invention by recombinant human CES1 were determined using an HPLC assay. Recombinant human CES1 (Gly18-Glu563, bearing a polyhistidine tag at the C-terminus) expressed in human cells and purified to homogeneity was obtained from Novoprotein, Summit, N.J., USA (catalogue number C450). Reactions were run in 384 well plates at 20° C. in a buffer of 50 mM sodium phosphate pH 7.5/100 mM NaCl. Assays used a fixed concentration of test compound (50 µM) and CES1 (50 nM) and a time course of the reaction was obtained by stopping samples at increasing times by addition of formic acid to lower the pH. Stopped samples were subsequently analysed by HPLC to resolve product acid from unhydrolysed ester, using a 50×2 mm C18 5 µM reversed-phase column (Phenomenex Gemini) at a flow rate of 1 ml/min using a gradient of acetonitrile in water, containing 0.1% formic acid. Chromatogaphy was monitored using absorbance at 300 nm wavelength. The % of product formed was determined using integrated peak areas and used to determine the initial rate of the reaction. The specific activity of the CES1 against each test compound under these conditions (in units of µM/min/µM) was obtained by dividing the initial rate of the reaction by the CES1 concentration.

Results:

Example 1 had a mean rate of hydrolysis of 0.21 (µM of test compound hydrolysed per minute per µM of CES1) (n=2) in the above assay.

The invention claimed is:

1. A crystalline hydrate of (2S,3R)-isopropyl 2-(((2-(1,5-dimethyl-6-oxo-1,6-dihydropyridin-3-yl)-1-((tetrahydro-2H-pyran-4-yl)methyl)-1H-benzo[d]imidazol-5-yl)methyl)amino)-3-hydroxybutanoate edisylate, wherein said crystalline hydrate is a monohydrate.

2. The crystalline hydrate according to claim 1, which has an X-ray powder diffraction pattern (XRPD) substantially as shown in FIG. 1.

3. The crystalline hydrate according to claim 1, which has an X-ray powder diffraction pattern with specific peaks at 2θ values, ±0.1° 2θ experimental error, of 5.1, 7.9, 10.1, 11.3, 11.9, 12.9, 13.4, 14.2, 18.3, 20.3, 21.0 and 21.8 degrees.

4. The crystalline hydrate according to claim 1, which has a DSC thermogram substantially as shown in FIG. 2.

5. The crystalline hydrate according to claim 1, which has an onset of melting at about 223° C. as determined by DSC.

6. The crystalline hydrate according to claim 1, which has a FT Raman spectrum substantially as shown in FIG. 3.

7. A pharmaceutical composition comprising the crystalline hydrate according to claim 1, and one or more pharmaceutically acceptable excipients.

8. A pharmaceutical composition according to claim 7, further comprising one or more other therapeutically active agents.

9. A pharmaceutical composition comprising the crystalline hydrate according to claim 3, and one or more pharmaceutically acceptable excipients.

* * * * *